United States Patent
Gage et al.

(10) Patent No.: US 6,265,604 B1
(45) Date of Patent: Jul. 24, 2001

(54) (R)-3-HYDROXY-3-(2-PHENYLETHYL)-HEXANOIC ACID DERIVATIVES

(75) Inventors: James R. Gage, Portage; Robert Charles Kelly, Augusta; Bradley D. Hewitt, Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/514,087

(22) Filed: Feb. 28, 2000

Related U.S. Application Data

(62) Division of application No. 09/213,887, filed on Dec. 17, 1998, which is a continuation of application No. 09/146,406, filed on Sep. 3, 1998, now abandoned.
(60) Provisional application No. 60/058,618, filed on Sep. 11, 1997.

(51) Int. Cl.[7] .................................................. C07C 69/76
(52) U.S. Cl. ............................................. 560/60; 562/451
(58) Field of Search ................................ 560/60; 562/451

(56) References Cited

FOREIGN PATENT DOCUMENTS

| 1355 667 | 7/1971 | (FR) | ................................ C07D/7/16 |
|---|---|---|---|
| 1355 668 | 7/1971 | (FR) | ............................... C07D/13/10 |
| WO 94/11361 | 5/1994 | (WO) | ........................... C07D/309/38 |
| WO 95/14012 | 5/1995 | (WO) | ........................... C07D/309/32 |
| WO 95/30670 | 11/1995 | (WO) | ........................... C07D/309/32 |

OTHER PUBLICATIONS

S. Thaisrivongs, et al.: Journal of Medicinal Chemistry, vol. 39, No. 23, 1996, pp. 4630–4642, XP002088571, "Structure–Based Design of HIV Protease Inhibitors: 5,6–Dihydro–4–hydroxy–2–pyrones as Effective, Nonpeptidic Inhibitors".

Hanno Wild, Bayer AG, Chemistry Science Laboratories Pharma,—Tetrahedron Letters, vol. 34, No. 2, pp. 285–288 (1993)—Are 6–Acylamino Oxapenems Stable Compounds?

TM Judge, et al.—"Asymmetric Syntheses and Absolute Stereochemistry of 5,6–Dihydro–a–pyrones, A New Class of Potent HIV Protease Inhibitors"—J. Am. Chem. Soc. 1997, vol. 119, No. 15, 3627–3628.

S. Thaisrivongs, et al.: "Structure–Based Design of HIV Protease Inhibitors: Sulfonamide–Containing 5,6–Dihydro–4–hydroxy–2–pyrones as Non–Peptidic Inhibitors"—Journal of Medicinal Chemistry, vol. 39, No. 22, Oct. 25, 1996.

*Primary Examiner*—Amelia Owens
(74) *Attorney, Agent, or Firm*—Bruce Stein

(57) ABSTRACT

The compound of the present invention (R)-3-hydroxy-3-(2-phenylethyl)-hexanoic acid

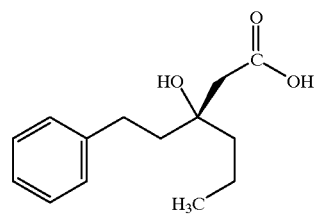

is an intermediate in the preparation of the anti-AIDS compound, [R-(R*,R*)]-N-[3-[1-5,6-dihydro-4-hydroxy-2-oxo-6-(2-phenylethyl)-6-propyl-2H-pyran-3-yl]propyl]phenyl]-5-(trifluoromethyl)-2-pyridinesulfonamide.

2 Claims, No Drawings

(R)-3-HYDROXY-3-(2-PHENYLETHYL)-HEXANOIC ACID DERIVATIVES

CROSS-REFERENCE TO RELATED APPLICATIONS

This application is a divisional of U.S. patent application Ser. No. 09/213,887 filed Dec. 17, 1998.

The present patent application is a continuation of U.S. patent application Ser. No. 09/146,406, filed Sep. 3, 1998 now abandoned which claims the benefit of U.S. provisional application Ser. No. 60/058,618 filed Sep. 11, 1997, under 35 USC §119(e)(i).

BACKGROUND OF THE INVENTION

1. Field of the Invention

The present invention is a novel process and novel intermediates to prepare [R-(R*,R*)]-N-[3-[1-[5,6-dihydro-4-hydroxy-2-oxo-6-(2-phenylethyl)-6-propyl-2H-pyran-3-yl]propyl]phenyl]-5-(trifluoromethyl)-2-pyridinesulfonamide (XIX) which is a protease inhibitor useful in treating humans infected with the HIV virus.

2. Description of the Related Art

[R-(R*,R*)]-N-[3-[1-[5,6-Dihydro-4-hydroxy-2-oxo-6-(2-phenylethyl)-6-propyl-2H-pyran-3-yl]propyl]phenyl]-5-(trifluoromethyl)-2-pyridinesulfonamide (XIX) can be produced by the process set forth in International Publications WO95/30670 and WO94/11361.

J. Med. Chem., 39(22), 4349 (1996) discloses the cyclic ester (VI) but in the racemic form. This document also discloses the transformation of the cyclic ester (VI) to the protease inhibitor (XIX) but by a different synthetic pathway.

J. Am. Chem. Soc., 111, 3627 (1997) discloses the amino compound (XVIII).

Tetrahedron Letters, 34(2), 277–280 (1993) discloses a method for the conversion of a β-hydroxycarbonyl compound to a ring similar to that of formulas (VI) and (CVI). The β-hydroxycarbonyl compound in the prior art is a secondary alcohol and that in the present invention is a tertiary alcohol. In addition, the processes are completely different with the process of Tetrahedron Letters not being operable on the tertiary alcohols (IV) and (CIV) of the present invention.

J. Med Chem., 39(23), 4630–4642 (1996) discloses a method to make compounds similar to that of formulas (VI) and (CVI) but in racemic form from starting materials different from the present invention by an unrelated method.

International Publication WO95/14012 claims a cyclic compound similar to the cyclic compounds (VI), (XVII) and (XXV) of the present invention but in racemic form. The process of the present invention produces these compounds in optically pure form.

International Publication WO94/11361 discloses the cyclic ester (VI) but in racemic form.

Acta Chemica Scandinavica, B31, 671–678 (1977) discloses a number of 5,6-dihydro-2-pyranones including the 6-(2-phenylethyl) compound of formula 3a in Table 1.

SUMMARY OF THE INVENTION

Disclosed is (R)-3-hydroxy-3-(2-phenylethyl)hexanoic acid (IV) and pharmaceutically acceptable salts thereof.

Also disclosed is (6R)-5,6-dihydro-4-hydroxy-6-[1-(2-phenyl)ethyl]-6-propyl-2H-pyran-2-one.

Further disclosed is [3α(R),6(R)]5,6-dihydro-4-hydroxy-3-[1-(3-nitrophenyl)propyl]-6-[1-(2-phenyl)ethyl]-6-propyl-2H-pyran-2-one (XVII).

Additionally disclosed is (S)-methyl 3-(3-nitrophenyl)pentanoate.

Also disclosed is (3α(R),6(R)]5,6dihydro-4-hydroxy-3-[(Z)-1-(3-nitrophenyl)propenyl]-6-[1-(2-phenyl)ethyl]-6-propyl-2H-pyran-2-one.

Also disclosed is a process for the production of the hydroxy lactone of formula (CVI)

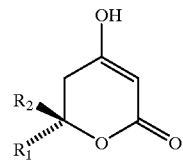

(CVI)

where $R_1$ is:

$C_1$–$C_6$ alkyl, cyclohexyl, phenyl,

—$CH_2$—$CH_2$—$\phi R_{1-1}$ where $R_{1-1}$ is

—OH (and protected froms thereof),

—$NH_2$ (and protected forms thereof),

—H,

—NH—CO—$CH_3$,

—N(—CO—$CH_3$)$_2$;

where $R_2$ is:

$C_1$–$C_6$ alkyl, cyclohexyl, phenyl,

—$CH_2$—$CH_2$—$\phi R_{2-1}$ where $R_{2-1}$ is

—OH (and protected froms thereof),

—$NH_2$ (and protected forms thereof),

—H,

—NH—CO—$CH_3$,

—N(—CO—$CH_3$)$_2$;

which comprises:

(1) contacting a salt of the formula (CIV)

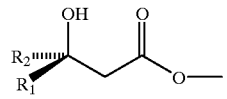

(CIV)

with an acid to produce a free acid, (2) extracting the free acid from the reaction mixture, (3) contacting the free acid with an activating agent, (4) contacting the reaction mixture of free acid/activating agent with malonate monoester and a divalent metal, (5) contacting the reaction mixture of step (4) with an acid, (6) contacting the reaction mixture of step (5) with a base in the presence of a $C_1$–$C_4$ alcohol, THF or DMF.

Further disclosed is a process for the production of the hydroxy lactone of formula (CVI)

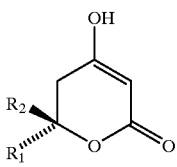

where $R_1$ is:
- $C_1$–$C_6$ alkyl,
- cyclohexyl,
- phenyl,
- —$CH_2$—$CH_2$—$\phi R_{1-1}$ where $R_{1-1}$ is
  - —OH (and protected froms thereof),
  - —$NH_2$ (and protected forms thereof),
  - —H,
  - —NH—CO—$CH_3$,
  - —N(—CO—$CH_3$)$_2$;

where $R_2$ is:
- $C_1$–$C_6$ alkyl,
- cyclohexyl,
- phenyl,
- —$CH_2$—$CH_2$—$\phi R_{2-1}$ where $R_{2-1}$ is
  - —OH (and protected froms thereof),
  - —$NH_2$ (and protected forms thereof),
  - —H,
  - —NH—CO—$CH_3$,
  - —N(—CO—$CH_3$)$_2$;

which comprises:
(1) contacting the anion of the formula (CIV)

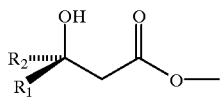

or the free acid form thereof with an activating agent,
(2) contacting the reaction mixture of free acid/activating agent with malonate monoester and a divalent metal,
(3) contacting the reaction mire of step (4) with an acid,
(4) contacting the reaction mixture of step (5) with a base in the presence of a $C_1$–$C_4$ alcohol, THF or DMF.

DETAILED DESCRIPTION OF THE INVENTION

The present invention is a novel process with novel intermediates to prepare [R-(R*,R*)]-N-(3-[1-[5,6-dihydro-4-hydroxy-2-oxo-6-(2-phenylethyl)-6-propyl-2H-pyran-3-yl]propyl]phenyl]-5-(trifluoromethyl)-2-pyridinesulfonamide (XIX) which is known to be a protease inhibitor and useful in treating humans infected with HIV.

CHART A discloses the transformation of the ketone (I) to the corresponding keto-ester (II), to the corresponding acid (III), to the corresponding salt (IV), to the corresponding keto-alcohol (V) and finally to the corresponding cyclic ester (VI); see also EXAMPLEs 1 thru 4 and the preferred method, EXAMPLE 18.

CHART B discloses the transformation of 4-chlorothiophenol (VII) to the corresponding chloroether (VIII), to the corresponding biphenyl compound (IX); see also EXAMPLEs 5 and 6.

CHART C discloses the condensation of the biphenyl compound (IX) with the salt (IV) to give the ester ether (X), and the transformations of the ester ether (X) to the corresponding alcohol (XI) and to the corresponding aldehyde (XII). Also disclosed is the coupling of the optically pure nitroester (XIII) with the aldehyde (XII) to produce the corresponding nitroether (XIV); see also EXAMPLEs 7 thru 10.

CHART D discloses the transformations of the nitroether (XIV) to the corresponding nitroketone (XV), to the corresponding nitroalcohol (XVI), to the corresponding nitro-α, β-unsaturated ester (XVII), to the corresponding amino compound (XVIII) and to the corresponding protease inhibitor (XIX); see also EXAMPLEs 11 thru 15.

CHART E discloses the preparation of the optically pure nitroester (XIII) which is used in CHART C. CHART E discloses the optical resolution of the racemic 1-(3-nitrophenyl)propanol (XX) to produce the corresponding optically pure 1-(3-nitrophenyl)propanol (XXI) and its transformation to the corresponding methylsulfonate (XXII), to the corresponding diester (XXIII), to the corresponding nitroacid (XXIV) and to the corresponding optically pure nitroester XIII); see also PREPARATIONS 1–5.

CHART F discloses an alternate, and preferable, route for the transformation of the cyclic ester (VI) to the corresponding nitro-α, β-unsaturated ester (XVII). The cyclic ester (VI) has the m-nitrophenyl adduct added to it to become the 6(R)-olefin (XXV), see EXAMPLE 16, which is hydrogenated with the appropriate catalyst to produce the reduced compound, the nitro-α,βunsaturated ester (XVII), see EXAMPLE 17. The nitro-α,β-unsaturated ester (XVII) is then transformed to the protease inhibitor (XIX) as previously discussed.

CHART G discloses a process to produce optically pure hydroxy lactones of formula (CVI). The process for the transformation of the salt of the formula (CIV) to the hydroxy lactone of formula (CVI) follows EXAMPLES 1 thru 4 and 18. The hydroxyl and amino groups of the starting material (CI) can be protected as is well known to those skilled in the art. These protecting groups can be removed at various places in the subsequent process steps, by means well known to those skilled in the art, or carried on thru to the product where they would be removed to produce the desired product. It is apparent to one skilled in the art there are numerous ways to produce the optically pure (CIV). It is not important how the resolution of EXAMPLE 3 producing the optically pure (CIV) is performed. The invention here is the conversion of the optically pure (CIV) to the optically pure (CVI).

The acid (III) forms base addition salts when reacted with bases of sufficient strength. The pharmaceutically acceptable salts include both inorganic and organic bases. The pharmaceutically salts are preferred over the free acids since they produce compounds which are more water soluble and more crystalline. The preferred pharmaceutically acceptable salts include salts of the following bases, for example, hydroxide, ammonia, tromethamine (THAM), 2-amino-2-(hydroxymethyl)-1,3-propanediol, (1R,2S)-norephedrine, (1S,2R)-norephedrine, (R)-2-amino-2-phenylethanol, (S)-2-amino-2-phenylethanol, (R)-1-phenylethylamine and (S)-1-phenylethylamine. It is preferred that the salt be the (1R, 2S)-norephedrine salt.

[R-(R*,R*)]-N-[3-[1-[5,6-Dihydro-4-hydroxy-2-oxo-6-(2-phenylethyl)-6-propyl-2H-pyran-3-yl]propyl]phenyl]-5-(trifluoromethyl)-2-pyridinesulfonamide (XIX) the compound of EXAMPLE 15 (COMPOUND) is known to be useful in treating humans infected with HIV, see International Publications WO95/30670 and WO94/11361. This COMPOUND inhibits retroviral proteinases and thus inhibit the replication of the virus. The COMPOUND of the present invention is useful in inhibiting human retroviral protease. The COMPOUND is useful for treating human patients infected with a human retrovirus, such as human immunodeficiency virus (strains of HIV-1 or HIV-2) or human T-cell leukemia viruses (HTVL-I or HTVL-II) which results in acquired immunodeficiency syndrome (AIDS) and/or related diseases.

Patients to be treated would be those individuals (1) infected with one or more strains of a human retrovirus as determined by the presence of either measurable viral antibody or antigen in the serum and (2) in the case of HIV, having either an asymptomatic HIV infection or a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4+ lymphocyte count of less than 500/mm$^3$ in the peripheral blood. Treatment would consist of maintaining an inhibitory level of the COMPOUND according to this invention in the patient at all times.

The COMPOUND of the present invention is useful for treating patients infected with human immunodeficiency virus (HIV) which results in acquired immunodeficiency syndrome (AIDS) and related diseases. For this indication, there compounds may be administered by oral, intranasal, transdermal, subcutaneous and parenteral (including intramuscular and intravenous) routes in doses of 0.1 mg to 100 mg/kg of body weight per day. It is preferred that the ccc be administered orally.

Those skilled in the art would know how to formulate the COMPOUND into appropriate pharmaceutical dosage forms. Examples of the dosage forms include oral formulations, such as tablets or capsules, or parenteral formulations, such as sterile solutions.

When the compound in this invention is administered orally, an effective amount is from about 0.1 mg to about 100 mg per kg of body weight per day. It is preferred that the effective amount is from about 10 to about 100 mg per kg of body weight per day. It is more preferred that the amount be from about 30 mg to about 90 mg per kg of body weight. It is preferred that the ccc be administered 2 to 5 times daily, more preferrably 3 times daily. It is preferred that the dose be from about 2,700 mg/day to about 4,500 mg/day.

Either solid or fluid dosage forms can be prepared for oral administration. It is preferred the ccc be given in solid dosage form, more preferably as a capsule.

When the compounds of this invention are administered parenterally, they can be given by injection or by intravenous infusion. An effective amount is from about 0.1 mg to 100 mg per kg of body weight per day. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition and/or other clinical symptoms specific to the patient to be treated.

DEFINITIONS AND CONVENTIONS

The definitions and explanations below are for the terms as used throughout this entire document including both the specification and the claims.

DEFINITIONS

All temperatures are in degrees Centigrade.

TLC refers to thin-layer chromatography.

HPLC refers to high pressure liquid chromatography; 4.6×250 mm Zorbax C-8 column, mobile phase A=methanol, mobile phase B=6.5 g t-butyl ammonium hydroxide in water, ph to 4.0 with acetic acid, gradient from 65/35 A/B to 70/30 A/B over 20 min, then isocratic 70/30 A/B for 5 min, then gradient to 90/10 A/B over 20 min; flow rate is 1.0 ml/min; UV detection at 254 nm.

THF refers to tetrahydrofuran.

DMF refers to dimethylformamide.

MTBE refers to methyl t-butyl ether.

DMSO refers to dimethylsulfoxide.

Saline refers to a saturated aqueous sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

COMPOUND refers to [R-(R*,R*)]-N-[3-[1-[5,6-dihydro-4-hydroxy-2-oxo-6-(2-phenylethyl)-6-propyl-2H-pyran-3-yl]propyl]-phenyl-]5-(trifluoromethyl)-2-pyridinesulfonamide (XIX).

Alkyl refers to $C_1$–$C_4$ alkyl including both straight and branched chain isomers.

$W_1$ refers to ethyl and t-butyl.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Resolution Of (±)-1-(3-nitrophenyl)propanol (XX) By Conversion To (S)-1-(3-nitrophenyl)propanol (XXI) and (R)-1-(3-nitrophenyl)propanol acetate Celite supported PS-30 lipase (Amano, 24 g) and isopropenylacetate (22.00 ml, 0.20 mol) is added to (±)-1-(3-nitrophenyl)propanol (XX, 24.00 g, 0.13 mol) in MTBE (240 mL). The mixture is stirred at 20–25° for 2 days. At the end of this time the catalyst is removed by filtration, the catalyst cake washed with ether, and the the mixture concentrated under reduced pressure to give an acetate-alcohol mixture. Separation of the mixture by silica gel chromatography gives (R)-1-(3-nitrophenyl)propanol acetate (13.03 g), $[\alpha]_D=+68.7°$ (ethanol, c=1) and (S)-1-(3-nitrophenyl) propanol (10.7 g), $[\alpha]_D=33.0°°$ (ethanol, c=1).

PREPARATION 2

(S)-1-(3nitrophenyl)propanol mesylate (XXII)

Diisopropylethylamine (1.07 g, 8.3 mmol) is added to a mixture of (S)-1-(3-nitrophenyl)propanol (XXI, PREPARATION 1, 1 g, 5.5 mmol) in methylene chloride (20 mL). The mixture is cooled to −20° and methanesulfonyl chloride (0.69 g, 6.02 mmol) is added. The reaction is held at −20° for 10 min, then held at 0° for 40 min. The reaction is diluted with methylene chloride, sodium bicarbonate (5%) is added and the phases are separated. The methylene chloride is evaporated to give the title compound, $[\alpha]_D=-79.9°$ (ethanol, c=1); TLC (silica gel GF, ethyl acetate/hexane, 20/80) $R_f=0.19$; NMR (CDCl$_3$, TMS) 0.96–1.01, 1.88–2.17, 2.89, 5.54–5.59, 7.57–7.62, 7.70–7.73 and 8.20–8.24 δ.

PREPARATION 3

(S)-Dimethyl 1-[1-(3-nitrophenyl)propyl]malonate (XXIII)

A solution of sodium ethoxide (1.0 M) is prepared by dissolving sodium metal (1.27 g, 0.055 mol) in absolute ethanol (55 mL). Diethyl malonate (8.84 g, 0.055 mol) is added to the above solution at 0°. (S)-1-(3-nitrophenyl) propanol mesylate (XXII, PREPARATION 2, 1.43 g, 5.5 mmol) is added dropwise to the above solution of sodium malonate (6.4 mL, 6.4 mmol) at −20°. After 2 hr at 20–25°, an additional aliquot of sodium malonate (5 mL, 5.0 mmol) is added to the reaction and then stirred overnight at 20–25°. The reaction is concentrated and partitioned between ethyl acetate and hydrochloric acid (1 N). The organic phase is separated and the solvent removed to give crude product which is chromatographed (silica gel; ethyl acetate/hexane, 10/90) to give the title compound, $[\alpha]_D=+19.4°$ (ethanol, c=1); TLC (silica gel GF, ethyl acetate/hexane, 20/80) $R_f=0.48$; NMR (CDCl$_3$, TMS) 0.70–0.75, 0.96–1.00, 1.27–1.32, 1.56–1.88, 3.37–3.45, 3.65–3.69, 3.86–3.96, 4.21–4.28, 7.44–7.49, 7.54–7.57 and 8.08–8.11 δ.

PREPARATION 4

(S)-3-(3-Nitrophenyl)pentanoic Acid (XXIV)

(S)-Dimethyl 1-[1-(3-nitrophenyl)propyl]malonate (XXIII, PREPARATION 3, 0.73 g, 2.26 mmol) is refluxed in hydrochloric acid (6 N, 10 mL) for 18 hr. The reaction is cooled and extracted with ethyl acetate. The ethyl acetate phase is washed with water, separated and condensed to give the title compound, $[\alpha]_D=13.3°$ (methanol, c=1); TLC (silica gel GF, acetic acid/ethyl acetate/hexane, 2/20/80) $R_f=0.46$; NMR (CDCl$_3$, TMS) 0.78–0.83, 1.59–1.82, 2.59–2.78, 3.07–3.17, 7.44–7.54 and 8.04–8.10 δ.

PREPARATION 5

(±)-3-(3-Nitrophenyl)pentanoic acid methyl ester (XIII)

To a solution of (±)-3-(3-nitrophenyl)pentanoic acid (XXIV, 30.21 g, 135 mmol, in methanol (250 mL) is added concentrated sulfuric acid (0.6 mL). The resulting mixture is heated to reflux for 3 hours. Upon cooling, the mixture is partitioned between ethyl acetate and sodium bicarbonate (5% aqueous). The aqueous layer is separated and back-extracted with two additional portions of ethyl acetate. The combined organic phases are washed with saturated aqueous sodium chloride, dried over sodium sulfate, filtered and concentrated to give the title compound, TLC (silica gel GF) for acetic acid/ethyl acetate/hexane (2/20/80) $R_f=0.54$, for ethyl acetate/hexane (20/80) $R_f=0.54$; NMR (CDCl$_3$, TMS) 0.80, 1.56–1.83, 2.55–2.75, 3.05–3.2, 3.57, 7.4–7.55 and 8.03–8.12 δ.

PREPARATION 6

(S)-3-(3-Nitrophenyl)pentanoic acid methyl ester (XIII)

Following the general procedure of PREPARATION 5 and making non-critical variations but starting with (S)-3-(3-nitrophenyl)pentanoic Acid (XXIV, PREPARATION 4) the title compound is obtained.

Example 1

Ethyl-3-hydroxy-3-(2-phenylethyl)hexanoate (II)

To a solution of diisopropylamine (32.2 ml, 230 mmol) in tetrahydrofuran (240 ml) at −58° is added 2.63 M n-butyl lithium in hexane (87.4 ml, 230 mmol) over one hour. Ethyl acetate (21.4 ml, 220 mmol) is then added and the reaction mixture stirred for 1 hour during which time the reaction mixture was cooled to −70°. 1-Phenyl-3-hexanone (I, 35.2 g, 200 mmol) is added slowly over 30 minutes and the reaction mixture stirred cold for 1 hour. The mixture was quenched with aqueous ammonium chloride (100 ml) and warmed to 20–25°. The mixture is then acidified with hydrochloric acid (4 M). The desired product is extracted into methyl t-butyl ether dried over magnesium sulfate and concentrated to give the title compound, TLC $R_f=0.71$ (ethyl acetate/hexane, 30/70); NMR (CDCl$_3$) 7.28–7.12, 4.13, 3.60, 2.73–2.63, 2.50, 1.83–1.77, 1.58–1.53, 1.41–1.36, 1.24 and 0.93 δ; CMR (CDCl$_3$) 173.0, 143.2, 128.5, 128.4, 128.3, 128.1, 125.8, 72.8, 60.6, 42.9, 41.3, 30.1, 17.0, 14.6 and 14.2 δ; MS (CI, ammonia) m/z (relative intensity) 282 (100), 264 (63), 247 (10), 194 (13), 172 (5), 159 (5).

Example 2

3-Hydroxy-3-(2-phenylethyl)hexanoic acid (III)

Ethyl-3-hydroxy-3-(2-phenylethyl)hexanoate (II, EXAMPLE 1, 200 mmol) is dissolved in methanol (423 ml) and 2M sodium hydroxide (150 ml, 300 mmol) is added. The reaction mixture is stirred at 20–25° overnight. Methanol is removed and the remaining aqueous mixture is acidified with hydrochloric acid (4 M). The desired product is extracted into methyl t-butyl ether and dried over magnesium sulfate. The product is concentrated to give the title compound, TLC $R_f$=0.10 (ethyl acetate/hexane, 30/70); NMR (CDCl$_3$) 7.43–7.13, 2.77–2.62, 2.06, 1.87–1.76, 1.63–1.57, 1.45–1.31 and 0.93 δ; CMR (CDCl$_3$) 176.9, 141.9, 128.4, 128.3, 125.9, 73.4, 42.7, 41.4, 40.9, 31.9, 17.0 and 14.5 δ; MS (CI, ammonia) m/z (relative intensity) 254 (100), 236 (28), 218 (3), 194 (3), 159 (5).

Example 3

(R)-3-Hydroxy-3-(2-phenylethyl)hexanoic acid, (1R,2S)-norephedrine salt (IV)

3-Hydroxy-3-(2-phenylethyl)hexanoic acid (III, EXAMPLE 2, 2.83 g, 11.97 mmol adjusted for methyl t-butyl ether) is dissolved in acetonitrile (15 ml). (1R,2S)-Norephedrine (910 mg, 5.99 mmol, 0.5 equiv.) is added and the mixture stirred overnight at 20–25°. After approximately one hour, the product began to precipitate. The following morning the slurry was cooled to 0° for 1 hour before filtering to collect the hydroxyacid salt. The cake is washed with acetonitrile (9 ml cold) and dried under reduced pressure with heat to give the desired product.

This material (ca. 1.5 g) is slurried in acetonitrile (21 ml) and heated to 70° for 30 minutes. The resulting solution is gradually cooled to 20–25° as the product precipitates. After 2 hours at 20–25°, the product is collected by vacuum filtration, washed with acetonitrile (21 ml) and dried at 20–25° under reduced pressure.

Again, this material is slurried in acetonitrile (21 ml) and heated to 70° for 30 minutes. The resulting solution is gradually cooled to room 20–25° as the product precipitates. After 2 hours at 20–25°, the product is collected by vacuum filtration, washed with acetonitrile (21 ml) and dried at 20–25° under reduced pressure to give the title compound, mp=113–117°; NMR (methanol) 7.41–7.08, 5.18, 4.98, 3.15, 2.65–2.60, 2.34, 1.79–1.73, 1.56–1.52, 1.43–1.37, 1.06 and 0.92 δ; CMR (methanol) 181.4, 144.6, 142.2, 130.2–129.3, 127.6, 127.1, 74.5, 73.9, 54.0, 46.4, 43.6, 43.4, 31.9, 31.9, 18.6, 15.7 and 12.9 δ; MS (CI, ammonia) m/z (relative intensity) 388 (25), 303 (15), 254 (30), 236 (7), 152 (100); $[\alpha]^{25}_D$=16 (C=1.0, methanol).

Example 4

(6R)-5,6-dihydro-4-hydroxy-6-[1-(2-phenyl)ethyl]-6-propyl-2H-pyran-2-one (VI)

(R)-3-Hydroxy-3-(2-phenylethyl)hexanoic acid, (1R,2S)-norephedrine salt (IV, EXAMPLE 3, 81 g, 209 mmol) is converted to the free acid, (R)-3-hydroxy-3-(2-phenylethyl) hexanoic acid by slurrying the salt in ethyl acetate (810 ml) and adding hydrochloric acid (1 M, 810 ml). The free acid is extracted into the ethyl acetate and the ethyl acetate layer collected and concentrated to an oil. The free acid is then redissolved in tetrahydrofuran (490 ml) and the solution cooled to –100. Carbonyl-diimidazole (37.3 g, 230 mmol) is added and the reaction mixture stirred cold for 2 hours. Monoethyl malonate magnesium salt (65.9 g, 230 mmol) is added and the reaction mixture gradually warmed to 20–25° while stirring overnight. The reaction is quenched with hydrochloric acid (1 M, 490 ml) and the organic layer collected. The organic layer is washed with a sodium bicarbonate solution and concentrated to 294 ml containing (R)-ethyl 5-hydroxy-7-phenyl-5-propylheptanoate (V). A solution of sodium hydroxide (0.5 M, 460 ml, 230 mmol) is added to the concentrated solution and the resulting cloudy mixture stirred at 20–25° overnight. Methyl t-butyl ether is added and the aqueous layer collected. The aqueous phase is acidified with hydrochloric acid (4 M) and the product is extracted into methyl t-butyl ether. The methyl t-butyl ether layer is dried over sodium sulfate and concentrated to give the title compound, TLC $R_f$=0.22 (ethyl acetate/hexane, 50/50) δ;CMR (CDCl$_3$) 7.29–7.13, 3.39, 2.70, 2.71–2.62, 1.98–1.93, 1.74–1.66, 1.45–1.34 and 0.93 δ; CMR (CDCl$_3$) 176.89, 167.5, 140.4, 128.6, 128.4, 128.2, 128.2, 126.3, 83.2, 60.1, 47.1, 44.3, 40.7, 40.4, 29.6, 16.8 and 14.5 δ; MS (CI, ammonia) m/z (relative intensity) 278 (100), 254 (15), 236 (15), 217 (5), 195 (5), 159 (3).

Example 5

(4-Phenylphenoxy)(4-chlorothiophenoxy)methane (VIII)

To a slurry of paraformaldehyde (36.24 g, 1.21 mol, 1.58 equiv) in toluene (243 ml) at 22° is added aqueous hydrobromic acid (48.5 wt %, 652 ml, 5.86 mol, 7.68 equiv) with an endotherm to 18°. The resultant biphasic solution is warmed to 40° and a solution of 4-chlorothiophenol (VII, 138.81 g, 0.960 mol, 1.26 equiv) in toluene (116 ml) is added over ½ hour while maintaining 40–43° and rinsed in with toluene (50 ml). The mixture is then warmed to 50° and stirred 1 hour. The mixture is cooled to 10°, the phases separated, and the aqueous washed with toluene (250 ml). The combined organics are treated with ice water (500 ml), hexanes (350 ml) and the phases separated. The aqueous phase is then washed with toluene (200 ml) and the combined organic phases are dried over magnesium sulfate and concentrated to give crude bromomethylthio-4-chlorobenzene (268.01 g), NMR 7.43, 7.34, 4.79 δ; CMR 134.37, 132.05, 131.78, 129.46, 37.32 δ; HRMS (EI$^+$) calculated for C$_7$H$_6$BrClS=235.9063, found =235.9063.

To a solution of 4-phenylphenol (129.91 g, 0.763 mol, 1.00 equiv) in DMF (400 ml) at –10° is added a solution of potassium t-butoxide in THF (20 wt %, 429.40 g, 0.765 mol, 1.00 equiv) followed by THF (50 ml), while maintaining less than 5°. The mixture is concentrated to 557 g net weight and DMF (33 ml) added followed by the crude bromomethylthio-4-chlorobenzene prepared above with a free exotherm from 22° to 70°. The crude bromomethylthio-4-chlorobenzene is rinsed in with DMF (50 ml) and the resultant slurry stirred at 80° for ½ hour. The mixture is cooled to 22° and hexanes (400 ml) followed by water (500 ml) added. The precipitate is collected by vacuum filtration and washed with water (1500 ml) and methanol (300 ml) and dried in a nitrogen stream to give a solid (251.25 g). The solid is dissolved in methylene chloride (1 l) and dried over magnesium sulfate and washed with methylene chloride (200 ml). A constant volume concentration (1300–1800 ml) is then performed while adding a total of 1.35 l methanol and ending at 1344 g net weight. The resultant precipitate is collected at 20–25° by vacuum filtration, washed with methanol (1 l) and dried at 65° under reduced pressure to give the title compound, mp=99–101°; TLC ($R_f$=0.64, ethyl acetatec/hexanes, 1/9); HPLC (rt)=9.67 min; NMR (CDCl$_3$) 7.55–6.99 and 5.44 δ; CMR (CDCl$_3$) 155.99, 140.52, 135.28, 133.48, 132.06, 129.18, 128.75, 128.24, 126.90, 126.80, 116.34, 73.15 δ; MS (CI, NH$_3$) m/z (relative intensity) 346 (1.7), 344 (3.5), 328 (3.8), 326 (8.1), 201 (11), 200 (100).

Example 6

1-Chloromethoxy-4-phenylbenzene (IX)

To a mixture of (4-phenylphenoy)(4-chlorothiophenoxy) methane (VIII, (EXAMPLE 5, 176.45 g, 539.9 mmol) in methylene chloride (750 ml) at 21° is added a solution of sulfuryl chloride (73.32 g, 543.2 mmol, 1.01 equiv) in methylene chloride (150 ml) while maintaining <23° over 8 min. The mixture is stirred at 20° for 11 min then cooled to 3°. A mixture of cyclohexene (60.7 ml, 599 mmol, 1.11 equiv) in methylene chloride (100 ml) is added over 10 min at 3–5°, then warmed to 19° and stirred 10 min. The mixture is concentrated to 600 ml total volume and hexanes (500 ml) added. The mixture is concentrated to 500 ml and hexanes (300 ml) added. The resultant slurry is concentrated to 500 ml and pentane (1.3 l) added. The slurry is cooled to −50° and the precipitate collected by vacuum filtration and washed with −30° pentane (700 ml) and dried to give a solid (115.28 g). A portion (110.34 g) of the solid is dissolved in methylene chloride (200 ml). Hexanes (1 l) is added and the mixture concentrated to 949 g. Hexane (200 ml) is added and the mixture concentrated to 589 g. Hexane (500 ml) is added, the slurry cooled to −30°, the precipitate collected by vacuum filtration, washed with hexane (300 ml) and dried to give the title compound, mp 67–70; TLC $R_f$=0.68 (ethyl acetate/hexanes, 8/92); HPLC rt=6.45 min; NMR 7.80–7.13 and 5.89 δ; CMR (CDCl$_3$) 155.03, 140.34, 136.49, 128.78, 128.35, 127.10, 126.88, 116.39 and 77.16 δ; HRMS (EI$^+$) calculated for $C_{13}H_{11}ClO$=218.0498, found=218.0493.

Example 7

(R)-(4-phenylphenoxy)methyl-3-(2-phenylethyl)-3-[(4-phenylphenoxy)methoxy]hexanoate (X)

To a slurry of (R)-3-hydroxy-3-(2-phenylethyl)hexanoic acid (−)norephedrine salt (IV, EXAMPLE 4, 25.04 g, 64.62 mmol) in water (185 ml) and MTBE (185 ml) at 20–25° is added aqueous hydrochloric acid (37.5 wt %, 7.51 g, 77.24 mmol, 1.20 equiv), adjusting the pH from 8.04 to 1.30. The phases are separated and the aqueous phase is washed with MTBE (185 ml). The organic phases are dried over magnesium sulfate and concentrated. To the concentrate is then added toluene (77 ml), N,N-diisopropylethylamine (96 ml, 551 mmol, 8.53 equiv), and 1-chloromethoxy-4-phenylbenzene (IX, EXAMPLE 6, 71.88 g, 328.68 mmol, 5.09 equiv). The mixture is then warmed to 110° and stirred at 110–117° for 5 hrs. The mixture is cooled to 65° and methanol (800 ml) added. The resultant slurry is cooled to −30° and the product collected by vacuum filtration, washed with methanol (200 ml) and dried to give crude product. An analytical sample is obtained by chromatography (ethyl acetate/hexanes) followed by crystallization to give the title compound, mp=104.0–105.5°; TLC $R_f$=0.50 (15% ethyl acetate/hexanes); HPLC rt=13.8 min; NMR (CDCl$_3$) 7.51–7.04, 5.78, 5.32, 2.75, 2.64–2.58, 2.03–1.97, 1.78–1.72, 1.41–1.28 and 0.86 δ; CMR (CDCl$_3$) 169.38, 157.14, 156.14, 142.04, 140.71, 140.41, 135.85, 134.56, 128.75, 128.68, 128.35, 128.29, 128.09, 126.97, 126.81, 126.73, 125.78, 116.13, 87.34, 85.20, 80.40, 41.19, 38.80, 38.61, 29.73, 16.74, 14.35 δ; MS (CI, NH$_3$) m/z (relative intensity) 620 (1.7), 619 (7.8), 618 (19), 418 (13), 266 (100); $[\alpha]^{25}_D$=−4 (C=1.0, methylene chloride).

Example 8

(R)-3-(2-phenylethyl)-3-[(4-phenylphenoxy)methoxy]hexanol (XI)

To a slurry of crude (R)-(4-phenylphenoxy)methyl-3-(2-phenylethyl)-3-[(4-phenylphenoxy)methoxy]hexanoate (X, EXAMPLE 7, 56.5 wt %, 49.32 g, 46.38 mmol) in toluene (500 ml) is added a solution of diisobutylaluminum hydride in toluene (1.52 M, 85 ml, 129.2 mmol, 2.79 equiv) while maintaining −20°. The mixture is slowly warmed to 1° over 2.5 hrs, then stirred ½ hr. Acetone (8.0 ml, 108.5 mmol, 2.34 equiv) is added and the mixture cannulated into an 18° solution of citric acid monohydrate (136 g, 647.2 mmol, 14.0 equiv) in water (433 ml) with controlled exotherm to 28°, rinsing with toluene (100 ml). The mixture is stirred at 20–25° for 1.5 hrs and the insolubles removed by vacuum filtration, washing with toluene. The phases are separated in the filtrate and the aqueous phase is washed with toluene (2×300 ml). The organic phases are dried over magnesium sulfate, then washed with aqueous sodium hydroxide (0.5 M, 2×500 ml). The organic phases are concentrated to 137 g net weight and methanol (250 ml) is added. The resultant slurry is is concentrated and methanol (250 ml) is added. The mixture is again concentrated and methanol (250 ml) added. The slurry is cooled to −60° and the insolubles removed by filtration. The filtrate is concentrated 60 g net weight, hexane (500 ml) is added, and the mixture concentrated to 22 g net weight. Hexane (500 ml) is added and the mixture again concentrated to 40 g net weight. Methylene chloride (25 ml) is added followed by a slow addition of hexane (500 ml) and pentane (250 ml) with cooling to −55°. The product is collected by vacuum filtration, washed with pentane (200 ml) and dried in a nitrogen stream to give the desired product. An analytical sample is obtained by chromatography (ethyl acetate/hexane) followed by crystallization (methylene chloride/hexane) to give the title compound, mp=49–53°; TLC $R_f$=0.14 (15% ethyl acetate/hexane); HPLC rt=9.18 min; NMR (CDCl$_3$) 7.56–7.07, 5.36, 3.76–3.74, 2.63–2.58, 1.94–1.88, 1.70–1.65, 1.38–1.30, 0.93 δ; CMR (CDCl$_3$) 157.05, 142.25, 140.73, 134.68, 128.70, 128.42, 128.29, 128.21, 126.76, 125.85, 116.07, 87.05, 81.85, 58.89, 38.77, 38.60, 38.23, 29.90, 17.04, 14.62 δ; MS (CI, NH$_3$) m/z (relative intensity) 423 (2.3), 422 (9.9), 252 (100); $[\alpha]^{25}_D$=6 (C=1.0, methylene chloride).

Example 9

(R)-3-(2-phenylethyl)-3-[(4-phenylphenoxy)methoxy]hexanal (XII)

To a mixture of crude (R)-3-(2-phenylethyl)-3-[(4-phenylphenoxy)methoxy]hexanol (XI, EXAMPLE 8, 91.1 wt %, 15.40 g, 34.68 mmol) in methylene chloride (47 ml) at 0° is added a solution of potassium bromide (0.4057 g, 3.409 mmol, 0.098 equiv) and sodium bicarbonate (1.557 g, 18.53 mmol, 0.53 equiv) in water (20.5 ml) followed by 4-hydroxy-2,2,6,6-tetramethylpiperidinyloxy, free radical (0.3060 g, 1.776 mmol, 0.051 equiv.). Aqueous sodium hypochlorite (13.4 wt %/vol, 26.6 ml, 47.88 mmol, 1.38 equiv) is then added by syringe pump over 1 hr while maintaining 1–5°. A solution of sodium thiosulfate pentahydrate (0.5182 g, 2.088 mmol, 0.0602 equiv) in water (14 ml) is then added. The phases are separated at 0° and the aqueous phase is washed with 2×50 ml methylene chloride. The organic phases are immediately filtered through magnesol (50.25 g) and rinsed through with methylene chloride (400 ml). The extracts are concentrated to an oil (30 g) and hexane (500 ml) is added. The mixture is concentrated to 250 g net weight and hexane (100 ml) added. The mixture is concentrated to 186 g net weight and pentane (300 ml) added. The resultant slurry is cooled to −50° and the desired product collected by vacuum filtration, washed with −50° pentane (100 ml) and dried to give a solid, analytically pure to give the title compound, mp=47.0–48.5°; TLC $R_f$=0.41 (ethyl acetate/hexane, 10/90); HPLC rt=10.95 min; NMR (CDCl$_3$) 9.79, 7.53, 7.40, 7.26, 7.20–7.08, 5.40, 2.67, 2.65–2.56, 1.99, 1.76, 1.38, 0.93 δ; CMR (CDCl$_3$) 201.83, 156.90, 141.69, 140.68, 134.82, 128.72, 128.47, 128.29, 128.24, 126.77, 125.99, 116.03, 87.19, 80.36, 50.14, 39.21, 39.14, 29.74, 16.86, 14.45 δ; MS (CI, NH$_3$) m/z (relative intensity) 420 (3.5), 220 (100); [α]$^{25}_D$=14 (C=1.0, methylene chloride).

Example 10

(3S),(7R) 4-Carbomethoxy-3-(3-nitrophenyl)-7-(2-phenylethyl)-7-[(4-phenylphenoxy)methoxy]decan-5-ol (mixture of diastereomers at C-4 and C-5) (XIV)

To a mixture of (S)-methyl 3-(3-nitrophenyl)pentanoate also known as (S)-3-(3-Nitrophenyl)pentanoic acid methyl ester (XIII, PREPARATION 6, 3.78 g, 15.932 mmol) in THF (55 ml) at −80°, is added a solution of sodium hexamethyldisilazide in THF (0.935 M, 17.5 ml, 16.36 mmol, 1.027 equiv) over 7 min while maintaining −80 to −85°. The resultant mixture is then warmed to −74° and stirred at −74 to −76° for 18 min. The mixture is cooled to −90° and a solution of (R)-3-(2-phenylethyl)-3-[(4-phenylphenoxy)methoxy]hexanal (XII, EXAMPLE 9, 6.50 g, 16.147 mmol, 1.013 equiv) in THF is added over 10 min while maintaining −85 to −90°, and rinsed in with THF (20 ml). The mixture is then warmed to −71° and saturated aqueous ammonium chloride solution (90 ml) added, followed by water (90 ml) and MTBE (90 ml) and the mixture warmed to 20–25°. The phases are separated and the aqueous washed with MTBE (90 ml). The extracts are dried over magnesium sulfate, and concentrated to an oil. An analytical sample is obtained by chromatography (ethyl acetate/hexanes) to give the title compound, TLC R$_f$=0.16, 0.24 (ethyl acetate/hexanes, 10/90); HPLC rt=12.52, 12.68, 12.97 min; MS (electrospray, sodium acetate) m/z (relative intensity) 662.5 (100).

Example 11

(3S),(7R) 4-Carbomethoxy-3-(3-nitrophenyl)-7-(2-phenylethyl)-7-[(4-phenylphenoxy)methoxy]decan-5-one (mixture of diastereomers at C-4)

A solution of (3S),(7R) 4-carbomethoxy-3-(3-nitrophenyl)-7-(2-phenylethyl)-7-[(4-phenylphenoxy)methoxy]decan-5-ol (XIV, EXAMPLE 10, 11.12 g, 79.0 wt %, 13.73 mmol) in methylene chloride (530 ml) is added to a ground mixture of pyridinium chlorochromate (16.099 g, 74.685 mmol, 5.44 eq), sodium acetate (6.984 g, 85.14 mmol, 6.20 eq) and florisil (5.181 g) while maintaining less than 11°. The mixture is warmed to 21° and stirred at 20–25° for 20 hrs. The resultant slurry is filtered through magnesol (47.7 g) and rinsed with methylene chloride (375 ml). The filtrate is concentrated to an oil. An analytical sample of the title compound is obtained by chromatography (ethyl acetate/hexanes): TLC R$_f$=0.34 (ethyl acetate/hexanes, 10/90); HPLC rt=13.02, 13.23 min; NMR (CDCl$_3$) 8.05–8.01, 7.60–7.00, 5.37, 5.21, 4.03, 3.94, 3.75, 3.58–3.43, 3.39, 2.96, 2.78–1.37, 1.20, 0.91, 0.71–0.61 δ; CMR (CDCl$_3$) 200.89, 200.60, 168.29, 167.81, 157.10, 157.05, 148.38, 148.30, 143.58, 143.32, 141.99, 141.93, 140.73, 140.69, 135.29, 135.01, 134.78, 129.38, 129.23, 128.75, 128.45, 128.36, 128.23, 126.77, 125.91, 125.80, 122.96, 122.80, 122.04, 122.00, 116.16, 87.14, 86.92, 80.93, 80.44, 66.34, 65.92, 52.79, 52.35, 49.02, 48.62, 46.28, 46.20, 38.70, 38.51, 38.43, 37.99, 30.10, 29.52, 26.92, 26.71, 16.64, 16.39, 14.39, 14.16, 11.81, 11.58; MS (CI, ammonia) m/z (relative intensity) 656 (2.8), 655 (6.1), 136 (100).

Example 12

(3S),(7R) 4-carbomethoxy-7-hydroxy-3-(3-nitrophenyl)-7-(2-phenylethyl)-decan-5-one (mixture of diastereomers at C-4) (XVI)

To a mixture of (3S),(7R) 4-carbomethoxy-3-(3-nitrophenyl)-7-(2-phenylethyl)-7-[(4-phenylphenoxy) methoxy]decan-5-one (XV, EXAMPLE 11, 9.14 g, 83.7 wt %, 11.995 mmol) in THF (20 ml) at 23° is added a solution of sulfuric acid in methanol (0.524 M, 20 ml, 10.48 mmol, 0.87 eq). The mixture is allowed to stand at 23° for 22 hrs, then a solution of sodium bicarbonate (3.52 g, 41.90 mmol, 3.49 eq) in water (50 ml) is added, followed by MTBE (50 ml). The phases are separated and the aqueous is washed with MTBE (30 ml). The combined organics are washed with aqueous sodium hydroxide (0.5 M, 2×50 ml) at 5°, then water (2×10 ml), then twice with a mixture of saturated aqueous ammonium chloride (15 ml) and water (35 ml). The organics are dried on magnesium sulfate and concentrated to an oil. An analytical sample of the title compounds is obtained by chromatography (ethyl acetate/hexanes): TLC R$_f$=0.39 (ethyl acetatec/hexanes, 25/75); HPLC rt=8.15, 8.50 min; NMR (CDCl$_3$) 8.15–7.85, 7.48–7.01, 3.99, 3.92, 3.78, 3.50–3.39, 3.38, 3.32–1.21, 0.82 and 0.74–0.67 δ; CMR (CDCl$_3$) 205.20, 204.99, 168.00, 167.46, 148.38, 143.10, 142.04, 141.97, 135.23, 134.99, 129.47, 129.33, 128.46, 128.41, 128.28, 128.18, 125.85, 122.82, 122.58, 122.17, 73.83, 73.49, 66.63, 66.36, 52.92, 52.50, 50.79, 50.60, 46.25, 46.17, 41.57, 41.01, 40.83, 30.03, 29.60, 26.95, 17.05, 16.90, 14.55, 14.43, 11.74 and 11.47 δ.

Example 13

[3α(R),6(R)]5,6-dihydro-4-hydroxy-3-[1(3-nitrophenyl)propyl]-6-[1-(2-phenyl)ethyl]-6-propyl-2H-pyran-2-one (XVII)

A 4° solution of aqueous sodium hydroxide (1 M, 11.4 ml, 11.4 mmol, 1.89 equiv) in methanol (35 ml) is added to crude (3S),(7R) 4-carbomethoxy-7-hydroxy-3-(3-nitrophenyl)-7-(2-phenylethyl)-decan-5-one (mixture of diastereomers at C-4) (XVI, EXAMPLE 12, 73.3 wt %, 3.740 g, 6.018 mmol) and rinsed in with methanol (45 ml), while maintaining <5°. The mixture is vigorously stirred to dissolve the majority of the crude oil, then moderately stirred at 0–5° for 67 hrs. The mixture is cooled to −5° and hexanes (90 ml) are added. The phases are separated at <5° and the organic phase is washed at <5° with a mixture of methanol (50 ml) and water (7 ml). The pH of the combined aqueous phase is adjusted from 12.55 to 6.24 at <5° with acetic acid (1.52 g, 25.31 mmol, 4.21 equiv). The aqueous is phase is concentrated, extracted with methylene chloride (2×40 ml), dried over magnesium sulfate, and concentrated to give a crude product. To a sample of the crude product (0.401 g) is added ether (1.0 ml). The resultant slurry is cooled to −30° and the precipitate collected by vacuum filtration, washed with cold ether and dried in a nitrogen stream to give a the title compound, TLC R$_f$=0.49 (ethyl acetatec/hexanes, 1/1); HPLC rt=6.93 min; NMR (CDCl$_3$/CD$_3$OD, 1/1) 8.08, 7.80, 7.56, 7.22, 7.07–6.88, 3.98, 3.33–3.30, 2.50–2.37, 1.92–1.70, 1.58–1.50, 1.22–1.14, 0.76 and 0.72 δ, CMR (CDCl$_3$/CD$_3$OD, 1/1) 169.05, 166.66, 148.66, 147.79, 141.99, 135.30, 129.21, 129.02, 128.70, 126.55, 123.51, 121.23, 105.13, 81.39, 42.58, 40.39, 40.09, 36.76, 30.38, 24.95, 17.44, 14.54 and 13.04 δ.

Example 14

[3α(R),6(R)]3-[1-(3-Aminophenyl)propyl]-5,6-dihydro-4-hydroxy-6-[1-(2-phenyl)ethyl]-6-propyl-2H-pyran-2-one (XVIII)

To a solution of [3α(R),6(R)]5,6-dihydro-4-hydroxy-3-[1-(3-nitrophenyl)propyl]-6-[1-(2-phenyl)ethyl]-6-propyl-2H-pyran-2-one (XVII, EXAMPLE 13, 0.6993 g, 1.651 mmol) in THF (50 ml) is added palladium on carbon (5%, 50% water wet, 0.2574 g, 0.06048 mmol, 0.0366 equiv) and the mixture hydrogenated at 50 psi on a Parr shaker for 21 hrs. Celite (2.07 g) is added and the catalyst removed by vacuum filtration and rinsed with THF. The filtrate is concentrated to give the title compound, TLC $R_f$=0.45 (ethyl acetate/hexanes, 1/1); HPLC rt=5.18 min.

Example 15

[R-(R*,R*)]-N-[3-[1-[5,6-dihydro-4-hydroxy-2-oxo-6-(2-phenylethyl)-6-propyl-2H-pyran-3-yl]propyl] phenyl]-5-(trifluoromethyl)-2-pyridinesulfonamide (XIX)

To a mixture of [3α(R),6R]3-[1-(3-aminophenyl)propyl]-5,6-dihydro-4-hydroxy-6-[1-(2-phenyl)ethyl]-6-propyl-2H-pyran-2-one (XVIII, EXAMPLE 14, crude 0.555 g, 1.378 mmol based on title compounds XIX), in methylene chloride (3.10 ml), DMSO (0.100 ml, 1.409 mmol, 1.02 equiv) and pyridine (0.56 ml, 6.92 mmol, 5.02 equiv) is added the crude mixture of 5-(trifluoromethyl)-2-pyridinesulfonyl chloride in methylene chloride prepared above (5.23 ml, ~2.3 mmol based on thiol, ~1.7 equiv) at −25 to −30° over 2 hours, titrating with the 5-(trifluoromethyl)-2-pyridinesulfonyl chloride mixture to an HPLC endpoint of 1.4 area % residual [3α(R),6R]3-[1-(3-aminophenyl)propyl]-5,6-dihydro-4-hydroxy-6-[1-(2-phenyl)ethyl]-6-propyl-2H-pyran-2-one (XVIII, EXAMPLE 14). Aqueous hydrochloric acid (1 M, 6.2 ml, 6.2 mmol, 4.50 equiv) and ethyl acetate (5.2 ml) is added and the phases separated. The aqueous phase is washed with methylene chloride (10 ml) and the combined organic phases dried on magnesium sulfate and concentrated. This concentrate is loaded on a silica gel column (9.76 g silica gel) packed with ethyl acetate/hexanes (10/90) and the product eluted with the following ethyl acetate in hexanes mixtures (50 ml 10%, 100 ml 20%, 100 ml 30%, and 50 ml 40%). The eluent is combined and concentrated to an oil with an ethyl acetate chase. Ethyl acetate is added (5.2 ml) and the product precipitated by slow addition of heptane (15 ml). The resultant slurry is cooled to −30° and the precipitate collected by vacuum filtration, washed with a −30° mixture of ethyl acetate (1 ml) and heptane (4 ml) and dried in a nitrogen stream to give the title compound, mp=86–89°; TLC $R_f$=0.66 (ethyl acetate/hexane, 50/50); NMR (CD₃OD) 8.94, 8.19, 8.02, 7.25–6.97, 3.93, 2.68–2.52, 2.15–2.09, 1.96–1.64, 1.33, 0.88 and 0.83 δ; CMR (CD₃OD) 169.9, 167.0, 161.6, 148.1, 147.6, 142.8, 137.7, 137.0, 130.1, 129.5, 129.3, 127.0, 126.1, 124.2, 122.6, 120.3, 106.2, 81.9, 43.6, 40.5, 40.5, 37.4, 30.9, 25.8, 17.9, 14.7 and 13.3 δ; MS (CI, ammonia) m/z (relative intensity) 621 (1.7), 620 (5.4), 604 (1.1), 603 (3.4), 411 (12), 394 (12), 148 (100); IR (mull) 1596, 1413, 1359, 1326, 1177, 1149, 1074 and 720 cm$^{-1}$ (same solid state form as reference).

Example 16

[3α(R),6(R)]5,6-Dihydro-4-hydroxy-3-[(Z)-1-(3-nitrophenyl)propenyl]-6-[1(2-phenyl)ethyl]-6-propyl-2H-pyran-2-one (XXV, major component) and [3α(R),6R]5,6-dihydro-4-hydroxy-3-[(E)-1-(3-nitrophenyl)propenyl]-6-[1-(2-phenyl)ethyl]-6-propyl-2H-pyran-2-one (XXV, minor component)

(6R)-5,6-dihydro-4-hydroxy-6-[1-(2-phenyl)ethyl]-6-propyl-2H-pyran-2-one (VI, EXAMPLE 4, 50.0 g, 187 mmol) is combined with m-nitropropiophenone (33.5 g, 187.2 mmol) and 375 ml of THF. Pyridine is added (31.0 mL, 374 mmol), and the resultant mixture is stirred and cooled to below −5°. A solution is prepared by adding titanium tetrachloride (31 ml, 280 mmol) to 80 ml of toluene, and this solution is added to the mixture in a controlled manner to maintain the reaction temperature below 10°. Toluene (15 ml) is used to rinse in all of the titanium tetrachloride solution and at the end of this addition, the reaction mixture is warmed to between 35–45° and maintained in this range for about 16 hours. The reaction mixture is cooled to 0° and water (200 ml) is added in a single portion. This mixture is stirred until all solids dissolve. The mixture is warmed to at least 15° and then transferred to a separatory funnel using water (250 ml) and ethyl acetate (500 ml) to dilute the mixture. The aqueous layer is separated, removed, extracted with ethyl acetate (150 ml) and discarded. The primary organic layer is washed sequentially with hydrochloric acid (1 N, 2×150 ml), water (150 ml) and saturated sodium bicarbonate (150 ml). Each wash is extracted with the ethyl acetate (150 ml) extract prior to disposal. At this point the primary organic layer and the extract are combined and concentrated under reduced pressure to give a concentrate. The concentrate is then dissolved in methylene chloride (350 ml). This solution is extracted with a total of 500 ml of 1 N sodium hydroxide (4×50 ml, then 3×100 ml). The combined aqueous extracts are washed with a total of 500 ml of methylene chloride (4×50 ml, then 3×100 ml) and then treated with hydrochloric acid (3 N, 150 ml). The acidified mixture is extracted with methylene chloride (400 ml, then 6×100 ml) and the combined organic extracts are washed with water (200 ml) and then saline (200 ml). After drying further with anhydrous sodium sulfate, the mixture is filtered through a pad of magnesol and then concentrated under reduced pressure to give the mixture of title compounds, TLC $R_f$=0.18 for (Z)-isomer, 0.28 for (E)-isomer (ethyl acetate/hexane, 1/1); CMR (CDCl₃) 166.93, 166.53, 148.27, 142.53, 142.39, 140.96, 132.23, 132.12, 131.82, 131.74, 129.87, 129.12, 128.55, 128.14, 126.16, 121.67, 120.56, 101.09, 81.77, 39.78, 35.23, 29.73, 16.91, 15.75, 15.69 and 14.23 δ; MS (CI+NH₃) m/z (relative intensity) 439 (100), 422 (18), 409 (9), 392 (9), 278 (9), 194 (10), 136 (9).

Example 17

[3α(R),6(R)]5,6-dihydro-4-hydroxy-3-[1-(3-nitrophenyl)propyl]-6-[1-(2-phenyl)ethyl]-6-propyl-2H-pyran-2-one (XVII)

[3α(R),6(R)]5,6-Dihydro-4-hydroxy-3-[(Z)-1-(3-nitrophenyl)propenyl]-6-[1-(2-phenyl)ethyl]-6-propyl-2H-pyran-2-one (XXV, EXAMPLE 16, 4.24 g, 10 mmol) and [(1,5-cyclooctadiene)rhodium(I)-1,2-bis-(2R,5R)-dimethylphospholano)benzene]tetrafluoroborate (6.0 mg, 0.01 mmol) are combined in an inert atmosphere and dissolved in 20 ml of deoxygenated methanol. The atmosphere is replaced with hydrogen at a pressure of 80 psig or more and the reaction is warmed to 55° and stirred for 24 hours. At the end of this period, the reaction is cooled to 20–25° and the hydrogen is replaced with an inert atmosphere. The reaction mixture is concentrated under reduced pressure and the residue is crystallized from a methanol/water mixture (3/1) to give the title compound, TLC $R_f$=0.49 (ethyl acetate/hexanes, 1/1); HPLC rt=6.93 min; NMR (CDCl₃/CD₃OD, 1/1) 8.08, 7.80, 7.56, 7.22, 7.07–6.88, 3.98, 3.33–3.30, 2.50–2.37, 1.92–1.70, 1.58–1.50, 1.22–1.14, 0.76 and 0.72 δ; CMR (CDCl₃/CD₃OD, 1/1) 169.05, 166.66, 148.66, 147.79, 141.99, 135.30, 129.21, 129.02, 128.70, 126.55, 123.51, 121.23, 105.13, 81.39, 42.58, 40.39, 40.09, 36.76, 30.38, 24.95, 17.44, 14.54 and 13.04 δ.

Example 18

(6R)-5,6-dihydro-4hydroxy-6-[1-(2-phenyl)ethyl]-6-propyl-2H-pyran-2-one (CVI)

(R)-3-Hydroxy-3-(2-phenylethyl)hexanoic acid,(1R,2S)-norephedrine salt (CIV,180 g; 486 mmoles) is converted to (R)-3-hydroxy-3-(2-phenylethyl)hexanoic acid by slurrying the salt in methylene chloride (1100 ml) and adding hydrochloric acid (2M, 720 ml). The free acid is extracted into the methylene chloride and the mixture is azeotropicaliy dried by atmospheric distillation with incremental addition of methylene chloride (700 ml total). The free acid mixture (350 ml) is added to a slurry of carbonyl-diimidazole (90.5 g, 558 mmoles) in methylene chloride (80 ml) and pyridine (210 ml) at −10 to 0°. The mixture is warmed to 0° and stirred for an hour.

A slurry of malonate monoethyl ester magnesium salt is prepared by adding an acetone slurry of potassium malonate monoethyl ester (144 g, 846 mmoles in 350 ml of acetone) to a slurry of magnesium chloride (72 g, 756 mmoles) which has been prepared by the slow addition of acetone (250 ml) to a slurry of magnesium chloride in methylene chloride (100 ml.) The malonate salt preparation is completed by atmospheric distillation to a volume of 350 ml.

The (R)-3-Hydroxy-3-(2-phenylethyl)hexanoyl imidazole mixture, from the carbonyl-diimidazole activation, is added to the magnesium ethyl malonate slurry at 10–20°. The mixture is warmed to 20–25° and stirred for approximately 16 hours. The reaction is quenched with the addition of hydrochloric acid (5N, 850 ml.) Methylene chloride (125 ml) is added and the phases separated. The product containing organic layer is washed with hydrochloric acid (1N, 400 ml) and then saturated sodium bicarbonate solution (500 ml). The organic phase is concentrated under vacuum to about 200 ml, methanol (700 ml) is added, and the vacuum concentration continued to a final volume of 150 ml. To the methanolic solution of the (R)-ethyl 5-hydroxy-3-oxo-5-(2-phenylethyl)-octanoate is added a methanolic solution of potassium hydroxide (59.5 g of 85%; 902 mmoles dissolved in 200 ml of methanol) at 15–20°. The mixture is stirred for 16 hr at 20°. Water (350 ml) is added and the product containing aqueous layer is washed twice with methyl t-butyl ether (350 ml, each wash). The aqueous phase is acidified with hydrochloric acid (6 M, 220 ml) and the product is extracted with toluene (550 ml). The toluene mixture is washed with water (150 ml) and concentrated under reduced pressure to 200 ml. The product is crystallized by the addition of branched octane (approx. 400 ml in two portions allowing crystallization to occur between additions). On cooling, the product is isolated by vacuum filtration, washed with branched octane, and dried at 20–25° to give the title compound.

Example 19

5,6-dihydro-4-hydroxy-6-[1-(2-(4-substituted)phenyl)ethyl]-6-isopropyl-2H-pyran-2-ones (CVI)

Following the general procedure of EXAMPLES 1 thru 4 and making non-critical variations but starting with 4-hydroxy-, 4-amino-, 4-monoalkylamino or 4-dialkylamino-phenyl-2-methyl-3-pentanone (CI), the title compound is obtained.

Example 20

(6S)-5,6-dihydro-4-hydroxy-6-[1-(2-phenyl)ethyl]-6-phenyl-2H-pyran-2-ones (CVI)

Following the general procedure of EXAMPLES 1 thru 4 and making non-critical variations but starting with 1,3-diphenyl-1-propanone (CI), the title compound is obtained.

Example 21 t-Butyl-3-hydroxy-3-(2-phenylethyl)hexanoate (II)

Following the general procedure of EXAMPLE 1 and making non-critical variations, but using t-butyl acetate in place of ethyl acetate the title compounds is obtained. It is preferred that t-butyl acetate be used.

CHART A

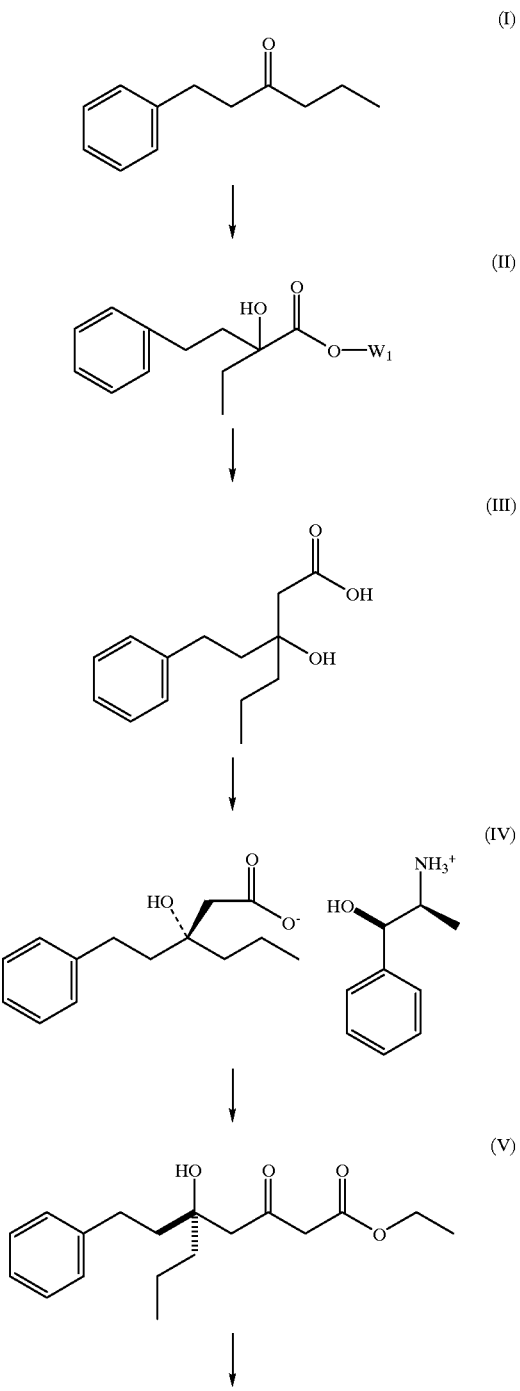

19
-continued
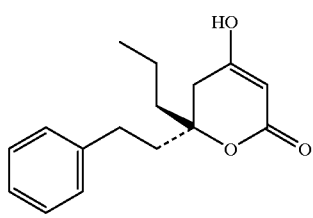
(VI)
CHART B
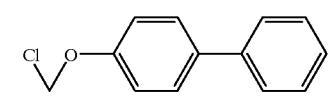
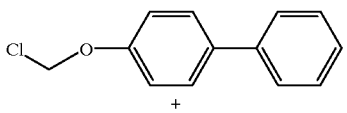
(VIII)
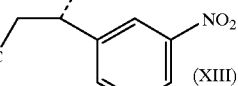
(IX)
CHART C
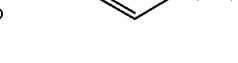
(IX)
+
20
-continued
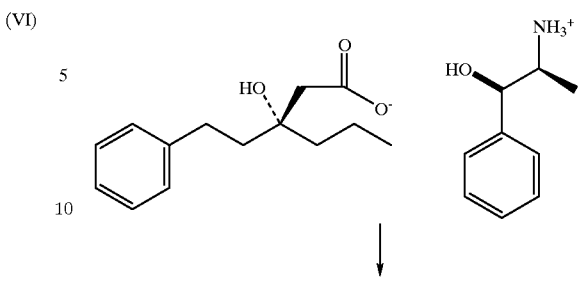
(IV)
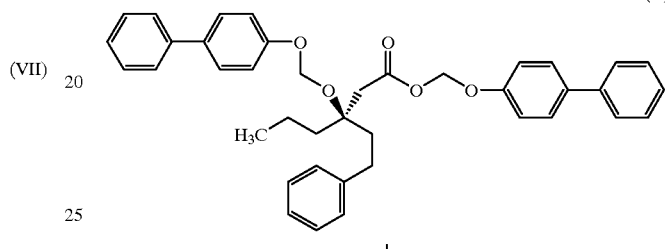
(X)
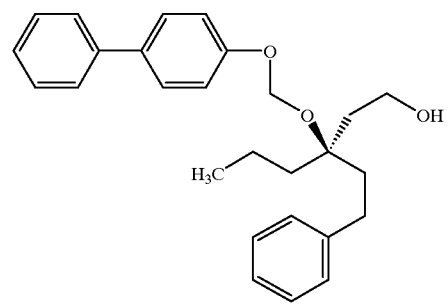
(XI)
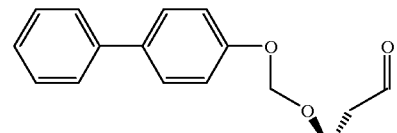
(XII)
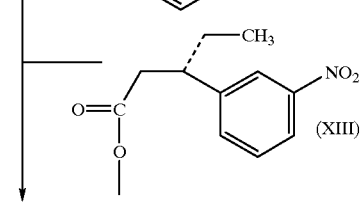
(XIII)

(XIV)
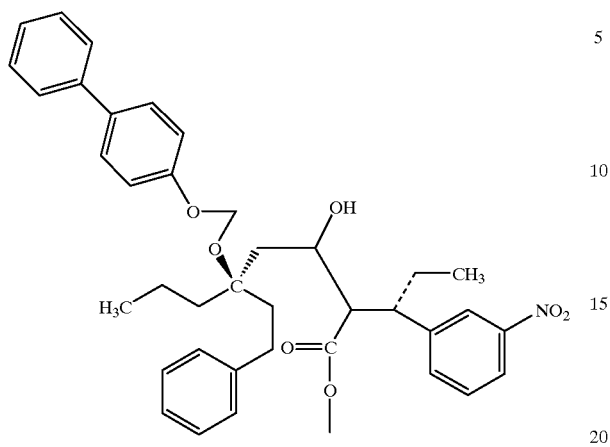
CHART D
(XIV)
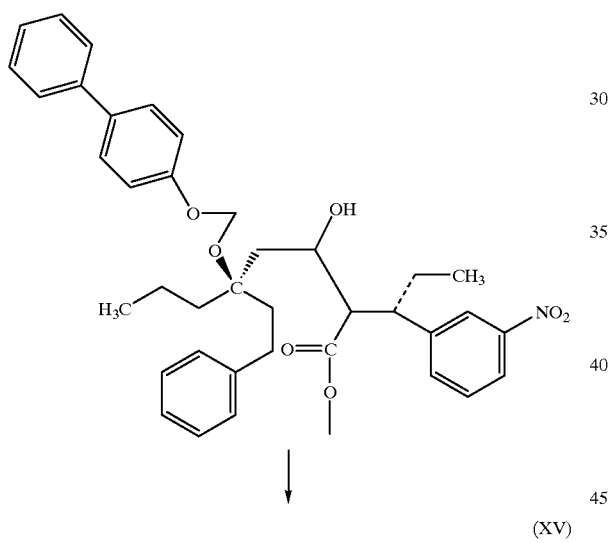
(XV)
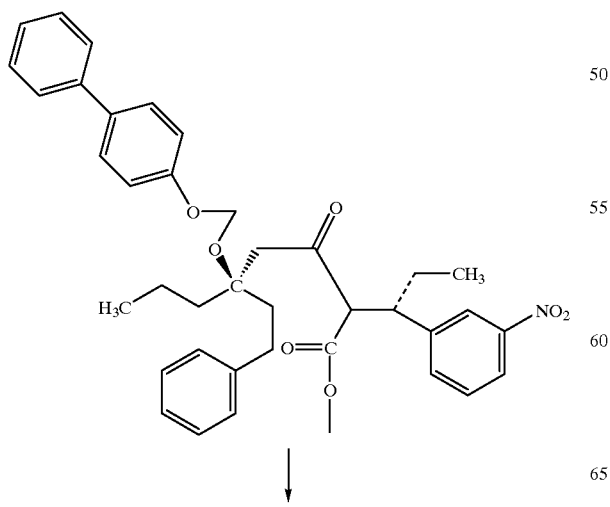
(XVI)
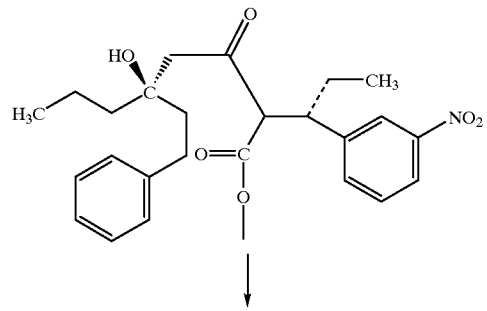
(XVII)
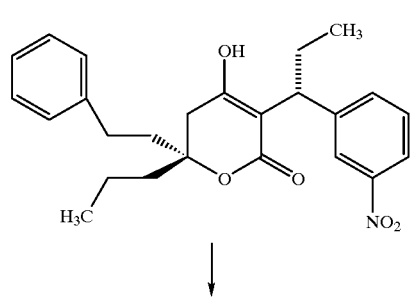
(XVIII)
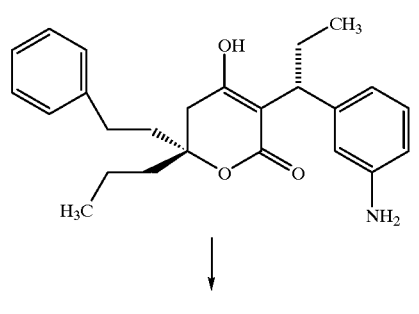
(XIX)
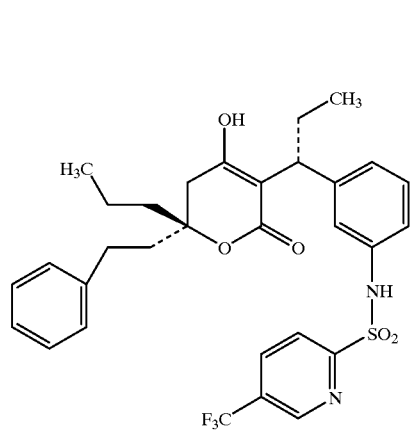

CHART E
(XX)
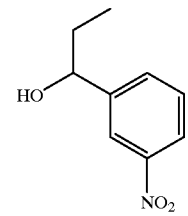
(XXI)
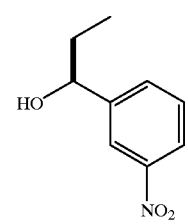
(XXII)
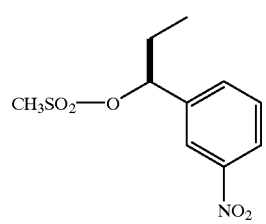
(XXIII)
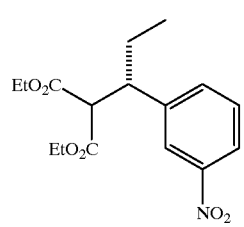
(XXIV)
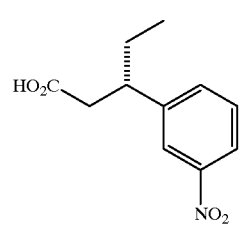
(XIII)
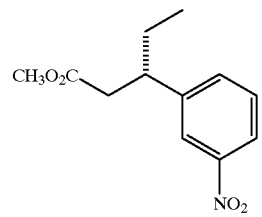
CHART F
(VI)
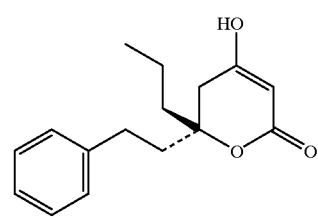
(XXV)
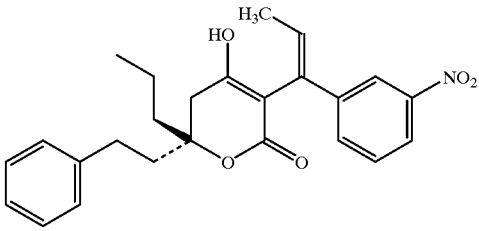
(XVII)
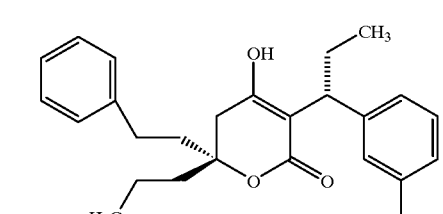
CHART G
(CI)
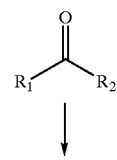

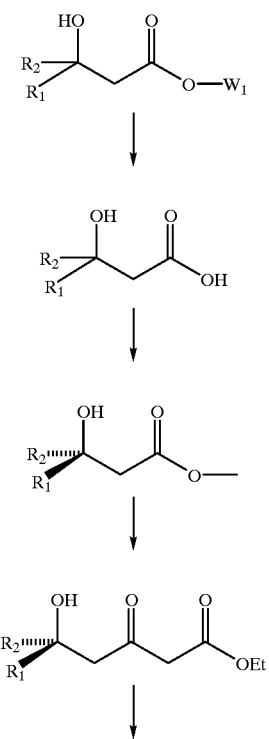
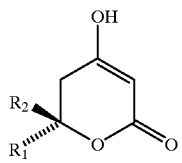
What is claimed is:
1. (R)-3-Hydroxy-3-(2-phenylethyl)hexanoic acid (IV) and salts thereof where the salts are selected from the group consisting of (1R,2S)-norephedrine, (1S,2R)-norephedrine, (R)-2-amino-2-phenylethanol, (S)-2-amino-2-phenylethanol, (R)-1-phenylethylamine and (S)-1-phenylethylamine.
2. A compound according to claim 1 which is (R)-3-hydroxy-3-(2-phenylethyl)hexanoic acid, (1R,2S)-norephedrine salt.
* * * * *